(12) United States Patent
Bien (10) Patent No.: US 11,918,320 B2
(45) Date of Patent: Mar. 5, 2024

(54) BIOMETRIC INFORMATION MEASUREMENT SYSTEM AND METHOD

(71) Applicant: UNIST (ULSAN NATIONAL INSTITUTE OF SCIENCE AND TECHNOLOGY), Ulsan (KR)

(72) Inventor: Franklin Don Bien, Ulsan (KR)

(73) Assignee: UNIST (ULSAN NATIONAL INSTITUTE OF SCIENCE AND TECHNOLOGY, Uljugun Ulsan (KR)

( * ) Notice: Subject to any disclaimer, the term of this patent is extended or adjusted under 35 U.S.C. 154(b) by 0 days.

(21) Appl. No.: 17/957,427

(22) Filed: Sep. 30, 2022

(65) Prior Publication Data

US 2023/0025214 A1    Jan. 26, 2023

Related U.S. Application Data

(63) Continuation of application No. PCT/KR2021/003841, filed on Mar. 29, 2021.

(30) Foreign Application Priority Data

Mar. 30, 2020 (KR) .................. 10-2020-0038203
Mar. 26, 2021 (KR) .................. 10-2021-0039556

(51) Int. Cl.
| | | |
|---|---|---|
| A61N 1/36 | (2006.01) | |
| A61B 5/00 | (2006.01) | |
| H02J 50/00 | (2016.01) | |
| H04W 4/80 | (2018.01) | |

(52) U.S. Cl.
CPC .......... *A61B 5/0031* (2013.01); *H02J 50/005* (2020.01); *H04W 4/80* (2018.02); *A61B 2560/0219* (2013.01); *H02J 2310/23* (2020.01)

(58) Field of Classification Search
CPC .......... A61B 2560/0219; A61B 5/0031; A61B 5/14532
See application file for complete search history.

(56) References Cited

U.S. PATENT DOCUMENTS 5,562,713 A * 10/1996 Silvian ............... A61N 1/37252
128/903
2020/0015722 A1    1/2020 Gopinathan et al.

FOREIGN PATENT DOCUMENTS

| KR | 10-2014-0139503 | 12/2014 |
|---|---|---|
| KR | 10-2018-0116302 | 10/2018 |
| KR | 10-1925632 | 11/2018 |
| KR | 10-2019-0086476 | 7/2019 |

(Continued)

OTHER PUBLICATIONS

International Search Report dated Jul. 12, 2021, issued in corresponding International Application No. PCT/KR2021/003841, filed Mar. 29, 2021, 7 pages.

(Continued)

*Primary Examiner* — Michael J D'Abreu
(74) *Attorney, Agent, or Firm* — CHRISTENSEN O'CONNOR JOHNSON KINDNESS PLLC (57) ABSTRACT

A biometric information measurement system and method are disclosed. A biometric information measurement system according to an embodiment of the present invention may comprise an implant device that is inserted into the human body so as to measure biometric information and an external device that transmits a signal to the implantable device while sweeping a frequency.

9 Claims, 10 Drawing Sheets

(56) References Cited

FOREIGN PATENT DOCUMENTS

| WO | WO-2013158667 A1 | * | 10/2013 | ............... | A61N 1/08 |
| WO | WO-2017116752 A1 | * | 7/2017 | ........... | A61B 5/0022 |

OTHER PUBLICATIONS

Written Opinion of the International Searching Authority dated Jul. 12, 2021, issued in corresponding International Application No. PCT/KR2021/003841, filed Mar. 29, 2021, 7 pages.

* cited by examiner

BIOMETRIC INFORMATION MEASUREMENT SYSTEM AND METHOD

CROSS-REFERENCES TO RELATED APPLICATIONS

This application is a continuation application of International Application No. PCT/KR2021/003841, filed Mar. 29, 2021, which claims the benefit of Korean Patent Application No. 10-2021-0039556, filed Mar. 26, 2021, and Korean Patent Application No. 10-2020-0038203, filed Mar. 30, 2020, the disclosures of which are incorporated herein by reference in their entirety.

BACKGROUND

1. Field of the Invention

Embodiments are related to a system and method for measuring biometric information.

2. Description of the Related Art

In order to manage diabetes developed in hundreds of millions of people worldwide, the most basic thing is to measure blood glucose. Accordingly, a blood glucose measurement device is an important diagnostic unit that is essential for a diabetic patient.

Various blood glucose measurement devices are recently developed, but the most common method is a method of gathering blood by sticking a finger and directly measuring a concentration of glucose within the blood. If an invasive method is used, there is a method of measuring blood glucose by inserting an invasive type sensor into the skin, measuring a concentration of glucose within blood for a given time, and making the concentration read by an external reader. In contrast, a non-invasive method includes a method using a light-emitting diode (LED)-photo diode (PD), etc. However, the non-invasive method has low accuracy due to an environmental factor such as sweat or a temperature, an alien substance, etc. because a sensor is attached to the skin.

The aforementioned information is merely for helping understanding, may include contents which do not form a part of the conventional technology, and may not include contents which may be presented to those skilled in the art through the conventional technology.

SUMMARY

Provided are a system and method for measuring biometric information, which can accurately measure blood glucose by measuring a characteristic change attributable to a change in the blood glucose through an implantable device and an external device.

Provided is a system for measuring biometric information including an implantable device inserted into a body and configured to measure biometric information and an external device configured to transmit a signal to the implantable device while sweeping a frequency.

According to an aspect, the biometric information may be measured based on a characteristic in which a resonance frequency is changed in response to permittivity around the implantable device.

According to another aspect, the implantable device may include an electro-magnetic (EM)-based sensor configured to reflect a signal transmitted by the external device, and a sensor interface configured to measure a power level of a signal reflected and returned by the EM-based sensor and convert the signal into digital data.

According to still another aspect, the sensor interface may include a frequency-selective filter configured to filter a frequency-selective characteristic based on a concentration of a target material around an inside of the body, and an envelope detector configured to find and output a minimum value in frequencies output by the frequency-selective filter.

According to still another aspect, the envelope detector is implemented to convert, into a direct current (DC) level, a signal reflected by S11 of S-parameters and to find a lowest point.

According to still another aspect, the sensor interface may further include an amplifier configured to adjust a size of the output of the envelope detector to a preset size or more, and an analog-digital converter (ADC) configured to receive an output of the amplifier and convert the output into the digital data.

According to still another aspect, the external device may include a wireless power transmitter for transmitting wireless power to the implantable device, and the implantable device may include a wireless power receiver for receiving wireless power transmitted by the external device.

According to still another aspect, the external device may include a phase-locked loop configured to sweep a frequency in order to drive an EM-based sensor included in the implantable device, and a power amplifier configured to provide power for driving the implantable device.

According to still another aspect, the external device may further include a data recovery module configured to recover digital data transferred by the implantable device.

According to still another aspect, the external device may further include a communication module for communicating with another external device.

According to still another aspect, the external device may further include at least one EM-based sensor configured to measure biometric information within a body outside the body.

There is provided a method of measuring biometric information including receiving a radio frequency (RF) signal having a specific frequency, which is transmitted by an external device, filtering, through a frequency-selective filter, a signal reflected by an electro-magnetic (EM)-based sensor included in an implantable device in response to a signal having a frequency swept, which is transmitted by the external device, converting the filtered signal into a direct current (DC) level through an envelope detector and finding a minimum value, converting the signal having the minimum value into digital data, and transmitting the digital data to the external device.

There is provided a method of measuring biometric information, including transmitting a signal to an implantable device while sweeping a frequency through a phase-locked loop in order to drive an electro-magnetic (EM)-based sensor included in an implantable device, providing power for driving the implantable device through a power amplifier, and receiving, from the implantable device, digital data converted from a signal having a minimum value detected by the implantable device, among signals reflected by the EM-based sensor, in response to the signal having the frequency swept.

In this case, according to embodiments of the present disclosure, blood glucose can be accurately measured by measuring a characteristic change attributable to a change in the blood glucose through the implantable device and the external device.

DETAILED DESCRIPTION

Hereinafter, embodiments are described in detail with reference to the accompanying drawings. However, the embodiments may be changed in various ways, and the scope of right of this patent application is not limited or restricted by such embodiments. It is to be understood that all changes, equivalents and substitutions of the embodiments are included in the scope of right.

Terms used in embodiments are merely used for a description purpose and should not be interpreted as intending to restrict the present disclosure. An expression of the singular number includes an expression of the plural number unless clearly defined otherwise in the context. In this specification, it should be understood that a term, such as "include" or "have", is intended to designate the presence of a characteristic, a number, a step, an operation, a component, a part or a combination of them described in the specification, and does not exclude the existence or possible addition of one or more other characteristics, numbers, steps, operations, components, parts, or combinations of them in advance.

All terms used herein, including technical or scientific terms, have the same meanings as those commonly understood by a person having ordinary knowledge in the art to which an embodiment pertains, unless defined otherwise in the specification. Terms, such as those commonly used and defined in dictionaries, should be construed as having the same meanings as those in the context of a related technology, and are not construed as being ideal or excessively formal unless explicitly defined otherwise in the specification.

Furthermore, in describing the present disclosure with reference to the accompanying drawings, the same component is assigned the same reference numeral regardless of its reference numeral, and a redundant description thereof is omitted. In describing an embodiment, a detailed description of a related known art will be omitted if it is deemed to make the subject matter of the embodiment unnecessarily vague.

Furthermore, in describing elements of an embodiment, terms, such as a first, a second, A, B, (a), and (b), may be used. Such terms are used only to distinguish one component from another component, and the essence, order, or sequence of a corresponding component is not limited by the terms. When it is said that one component is "connected", "combined", or "coupled" to another component, the one component may be directly connected or coupled to another component, but it should also be understood that a third component may be "connected", "combined", or "coupled" between the two components.

A component included in any one embodiment and a component including a common function are described using the same name in another embodiment. Unless described otherwise, a description written in any one embodiment may be applied to another embodiment, and a detailed description in a redundant range is omitted.

Figure 1:
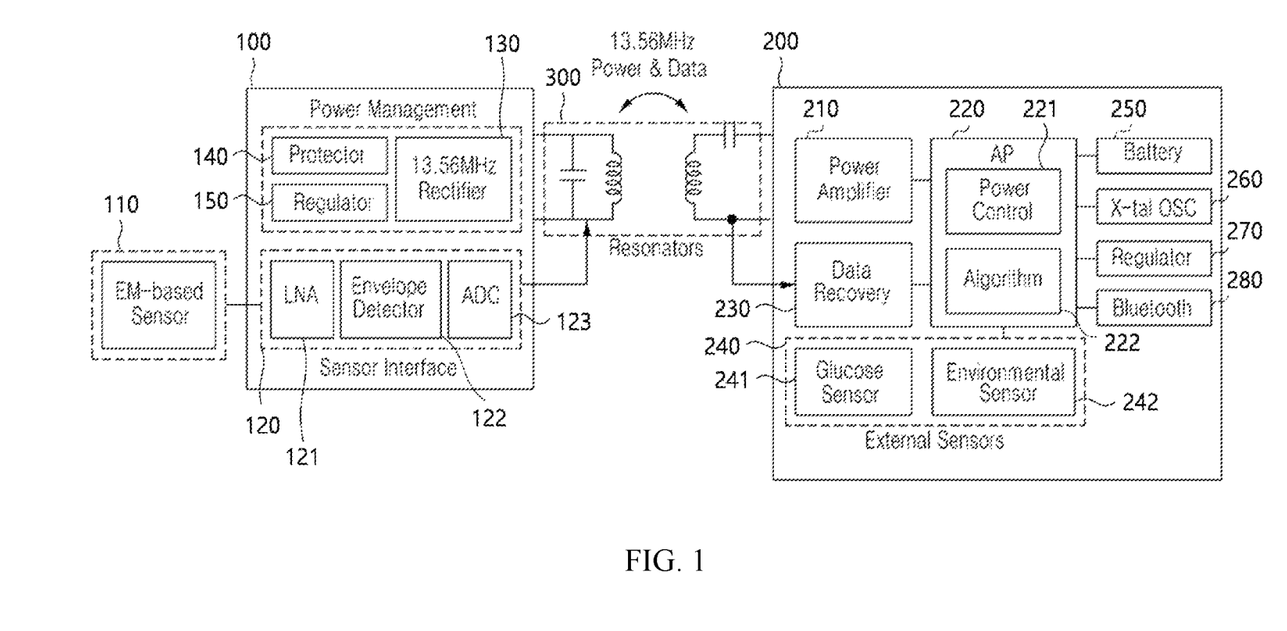
FIG. 1 is a diagram illustrating an example of a system for measuring biometric information according to an embodiment of the present disclosure.

FIG. 1 is a diagram illustrating an example of a system for measuring biometric information according to an embodiment of the present disclosure. The system for measuring biometric information according to the present embodiment may include an implantable device 100 and an external device 200.

The implantable device 100 including an electro-magnetic (EM)-based sensor 110 fabricated to measure biometric information in an interstitial fluid is disposed under the skin, and has a characteristic in which a resonance frequency thereof is changed in response to permittivity around the implantable device 100. In order to operate the EM-based sensor 110 included in the implantable device 100, a signal whose frequency is constantly changed needs to be injected. If such a signal is changed through the EM-based sensor 110, an sensor interface 120 for measuring the changed signal is required. Furthermore, the external device 200 may predict a change (e.g., a change in the concentration of blood glucose) in biometric information of an interstitial fluid through a change in coupling intensity based on a fringing field. In this case, the accuracy of measurement of biometric information may be supplemented by using several multi-modes using the implantable device 100 and the external device 200.

The implantable device 100 may include the sensor interface 120 for measuring a signal that is changed through the EM-based sensor 110, along with the EM-based sensor 110 fabricated to measure biometric information in an interstitial fluid. The sensor interface 120 may include a low-noise amplifier (LNA) 121, an envelope detector 122, and an analog-digital converter (ADC) 123. Such a sensor interface 120 is more specifically described with reference to FIG. 2.

The external device 200 may transfer power to the implantable device 100 through a resonator 300. Data transmission between the implantable device 100 and the external device 200 may also be performed by using the resonator 300. The resonator 300 may induce a wave or vibration having a specific frequency by using a resonant phenomenon between a first circuit (e.g., this is an electric circuit including a coil and a condenser and is a wireless power receiver) included in the implantable device 100 and a circuit (e.g., this is an electric circuit including a coil and a condenser and is a wireless power transmitter) included in the external device 200. In the embodiment of FIG. 1, a frequency of 13.56 MHz is described as being used, but the present disclosure is not limited thereto.

In this case, the implantable device 100 may further include a rectifier 130, a protector 140, and a regulator 150 in order to manage power transferred through the resonator 300. The rectifier 130 may be used to obtain DC power from AC power that is transferred through the resonator 300. The regulator 150 may be used to maintain a constant voltage. The protector 140 is an overvoltage protector, and may be used to prevent damage to the system due to high power in the implantable device 100 when power is transmitted by the external device 200.

As illustrated in FIG. 1, the external device 200 may include a power amplifier 210, an application processor (AP) 220, a data recovery module 230, an external sensor 240, a battery 250, an X-tal oscillator (OSC) 260, a regulator 270, and a Bluetooth module 280. The external sensor 240 may include an EM-based glucose sensor 241 that enables the external device 200 to directly measure biometric information and an environmental sensor 242 for measuring information (e.g., a temperature) on a surrounding environment. As an example of the EM-based glucose sensor 241, one or more EM-based sensors for measuring various types of biometric information may be included in the external sensor 240. The battery 250 may be used to supply power to the external device 200. The X-tal OSC 260 may be used to generate an accurate frequency. The regulator 270 may be used to maintain a constant voltage. The Bluetooth module 280 may be used to communicate with another external device, such as a smartphone. Bluetooth is only an example. Various communication protocols for communicating with another external device and communication modules corresponding to the communication protocols may be used. The AP 220 is a micro control unit (MCU), and may manage the transmission of required power or more (power control) by monitoring power of the implantable device 100 and the external device 200. Furthermore, the AP 220 may control data received from the Bluetooth module 280 and the external sensor 240, and may process data transferred by the implantable device 100. Such management of power or such control/processing of data may be performed according to an algorithm that is included in the AP. The data recovery module 230 may include an in-band data recovery system capable of recovering data transferred by the implantable device 100. For example, the implantable device 100 may modulate measured data into a signal of several hundreds to thousands of kHz through a modulation (LSK, FSK, OSK, etc.) method, and may then transmit the modulated data by carrying the modulated data on a signal of 13.56 MHz. In this case, the data recovery module 230 of the external device 200 may recover a signal for data by demodulating power that shows a normal power level after the power is reduced to a certain degree depending on data and filtering the signal of 13.56 MHz. In addition, the external device 200 may include a wireless power transmission system for the transfer of power for the driving of the implantable device 100.

Figure 2:
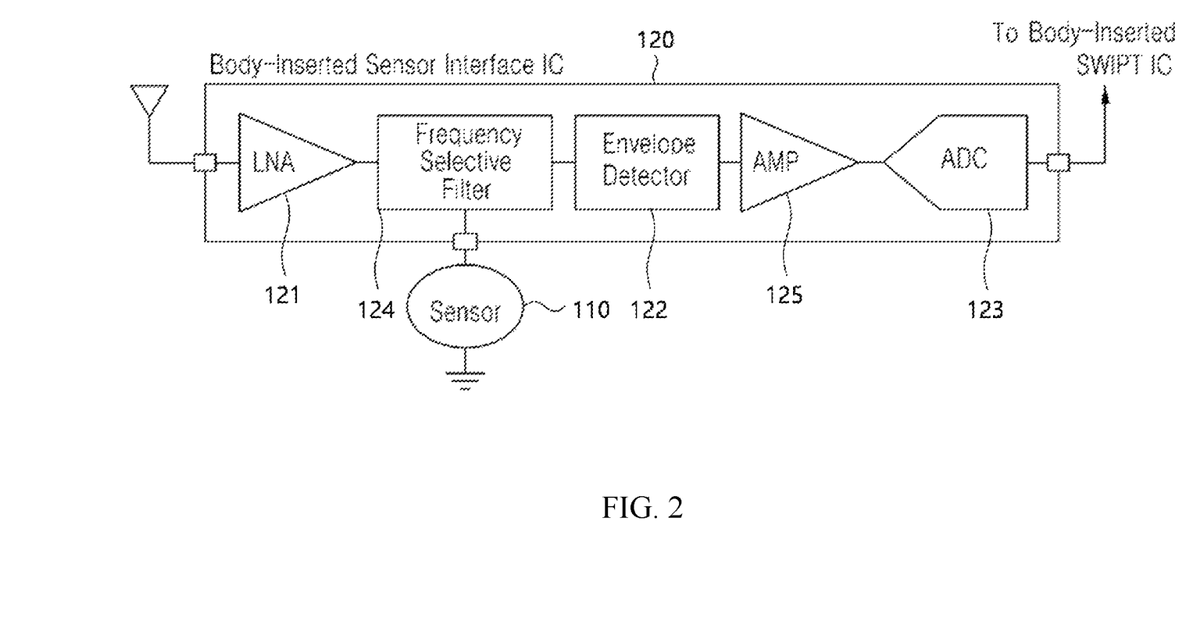
FIG. 2 is a diagram illustrating an example of an internal construction of an implantable device according to an embodiment of the present disclosure.

FIG. 2 is a diagram illustrating an example of an internal construction of the implantable device according to an embodiment of the present disclosure. The sensor interface 120 may measure an S-parameter characteristic of the EM-based sensor 110, that is, a power level of a radio frequency (RF) that is reflected and returned by the EM-based sensor 110, and may convert the measured S-parameter characteristic into digital data. The data converted into the digital data may be transmitted to the outside of the body (e.g., the external device 200) by the implantable device 100.

The sensor interface 120 may include the LNA 121, the envelope detector 122, and the ADC 123 as described above. In the embodiment of FIG. 2, the sensor interface 120 may further include a frequency-selective filter 124 and an amplifier (AMP) 125.

The LNA 121 may receive an RF signal that has a specific frequency and that is transmitted by the external device 200. The frequency-selective filter 124 has a frequency-selective characteristic according to a concentration of a target material (e.g., blood glucose) around the EM-based sensor 110 while operating in conjunction with the EM-based sensor 110 inserted into the skin, and may process a filter operation for the size of a signal that is reflected and returned by the EM-based sensor 110. The envelope detector 122 may find the lowest point by converting, into a direct current (DC) level, a signal reflected by S11 among S-parameters. The amplifier 125 may adjust the output of the envelope detector 122 suitably for the ADC 123. The ADC 123 may digitize an amplified signal and transmit the digitized signal to a simultaneous wireless information and power transfer (SWIPT) integrated circuit (IC). Such a SWIPT IC may be a circuit including the first circuit that is included in the implantable device 100, among the aforementioned rectifier 130, protector 140, regulator 150, and the resonator 300. The ADC 123 may be implemented to sufficiently handle a signal range of 30 dB or more, for example.

Figure 3:
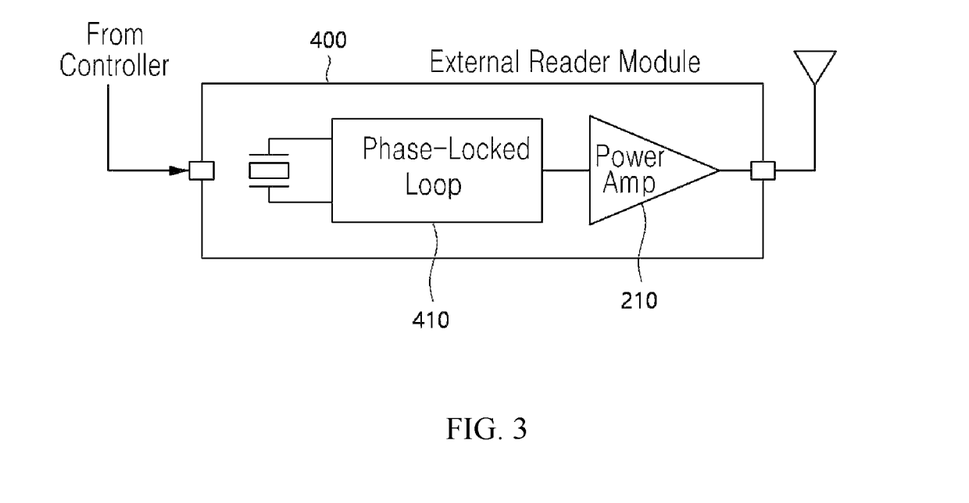
FIG. 3 is a diagram illustrating an example of an internal construction of an external device according to an embodiment of the present disclosure.

FIG. 3 is a diagram illustrating an example of an internal construction of the external device according to an embodiment of the present disclosure. An external reader module 400 may be included in the external device 200, and may include the power amplifier (AMP) 210 and a phase-locked loop 410. The external reader module 400 may include a frequency sweeping and driving circuit for driving the EM-based sensor 110 over a sufficient wide frequency band so that a change in the S-parameters characteristic of the EM-based sensor 110 included in the implantable device 100 can be measured. Accordingly, the phase-locked loop 410 that constitutes the external reader module 400 may process a frequency scan of the implantable device 100 that is inserted under the skin. The power amplifier 210 may provide power for the driving of the implantable device 100.

Figure 4:
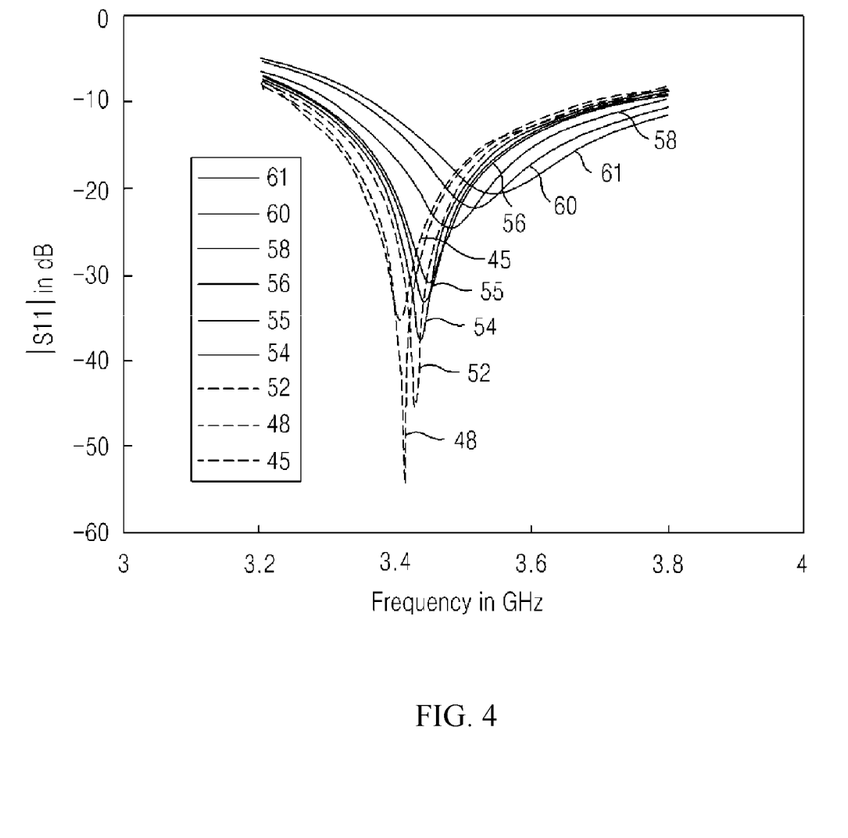
FIG. 4 is a graph illustrating response curves of S11 parameters of the implantable device according to an embodiment of the present disclosure.
Figure 5:
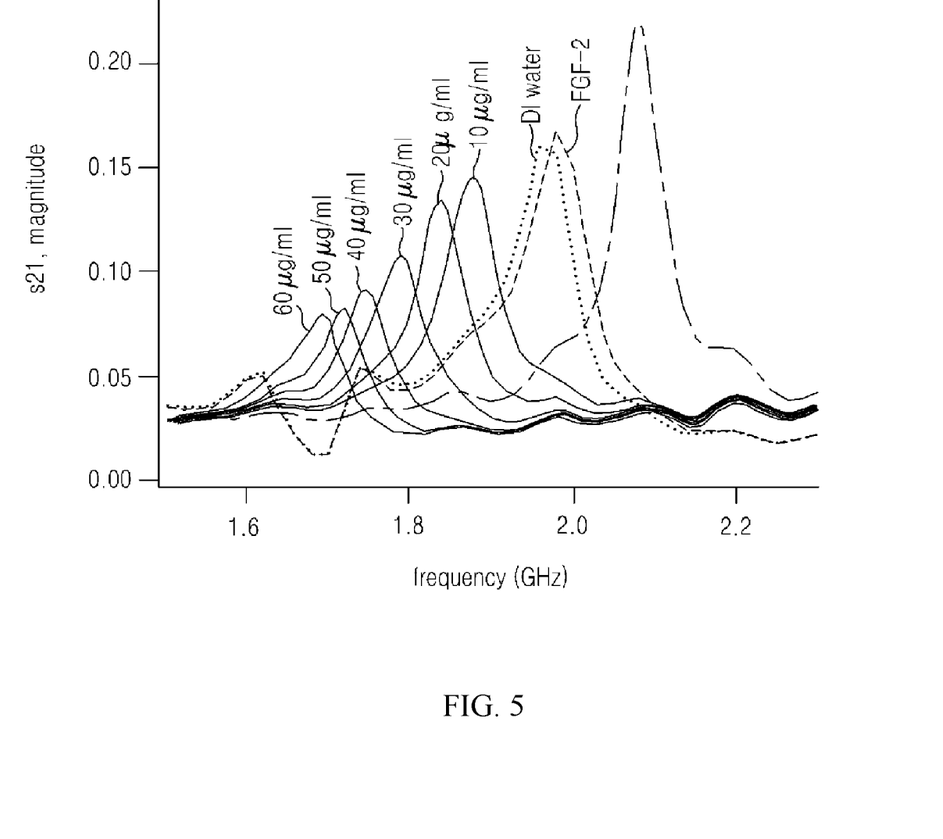
FIG. 5 is a graph illustrating response curves of S21 parameters of the external device according to an embodiment of the present disclosure.

FIG. 4 is a graph illustrating response curves of S11 parameters of the implantable device according to an embodiment of the present disclosure, and FIG. 5 is a graph illustrating response curves of S21 parameters of the external device according to an embodiment of the present disclosure.

Figure 6:
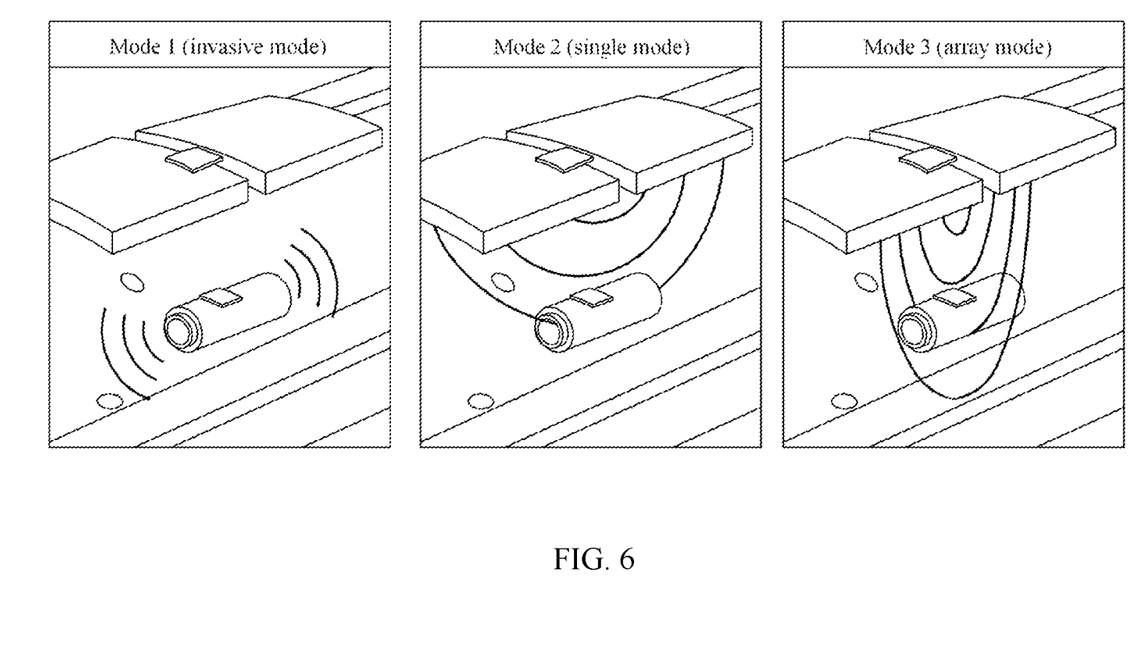
FIG. 6 is a diagram illustrating an operation of a system for measuring biometric information for each mode according to an embodiment of the present disclosure.

FIG. 6 is a diagram illustrating an operation of the system for measuring biometric information for each mode according to an embodiment of the present disclosure. Modes of The system for measuring biometric information may include three modes of an invasive mode, a single mode, and an array mode.

The invasive mode is a mode that plays a role to measure precise blood glucose among the three modes, and may be a mode for measuring a change in blood glucose spread into an interstitial fluid layer at intervals of 5 minutes through an ultra-small-sized EM sensor having a diameter of less than 3 mm, which may be inserted under the skin through a syringe. A sensor for the invasive mode scans electromagnetic waves around the sensor with a dense frequency over a broad band, and may precisely measure a change in permittivity according to a change in blood glucose through characteristic analysis of EM that is reflected for each frequency. Such an invasive mode may enable blood glucose to be accurately measured because influences, such a pressure, a temperature, humidity, and a movement upon measurement, are excluded compared to an EM-based non-invasive external-attachment type blood glucose sensor.

The single mode is a mode which has slightly lower precision than the invasive mode, but is responsible for the measurement of blood glucose in a wider area, and may be a mode for measuring a change in blood glucose in an interstitial fluid layer at intervals of 5 minutes, which is the same as the invasive mode, through an EM sensor that is attached to a surface of an extrasomatic skin. The single mode sensor is a non-invasive blood glucose sensing mode for measuring blood glucose through the analysis of a change in electromagnetic waves that penetrate the interstitial fluid layer based on a change in coupling between two EM sensors. That is, the single mode is slightly coarse, but determines an approximate range of blood glucose over a wide area (coarse scanning). The invasive mode finely scan within a determined range (fine scanning), and may implement heterogeneous sensor redundancy that enables the measurement of an accurate blood glucose value in a wide area that covers 40 to 600 mg/dl through the fusions of sensing information of Mode 1 and Mode 2.

The array mode is a mode which have very low precision, but plays a role to detect a danger of a change in blood glucose in real time when the change is great, and may be a mode for monitoring a change in blood glucose within a blood vessel disposed at a deeper place of an interstitial fluid layer in real time through an EM sensor that is attached to a surface of an extrasomatic skin. The array mode sensor may scan a sudden change in blood glucose within a blood vessel in real time based on the principle that the penetration depth of EM is increased by driving several EM sensors simultaneously in parallel. A blood glucose value in the interstitial fluid layer has time delay of about 5 to 20 minutes compared to an actual blood glucose value within a blood vessel. Accordingly, the array mode may implement the real-time measurement of blood glucose based on a change in the blood glucose within the blood vessel.

Figure 7:
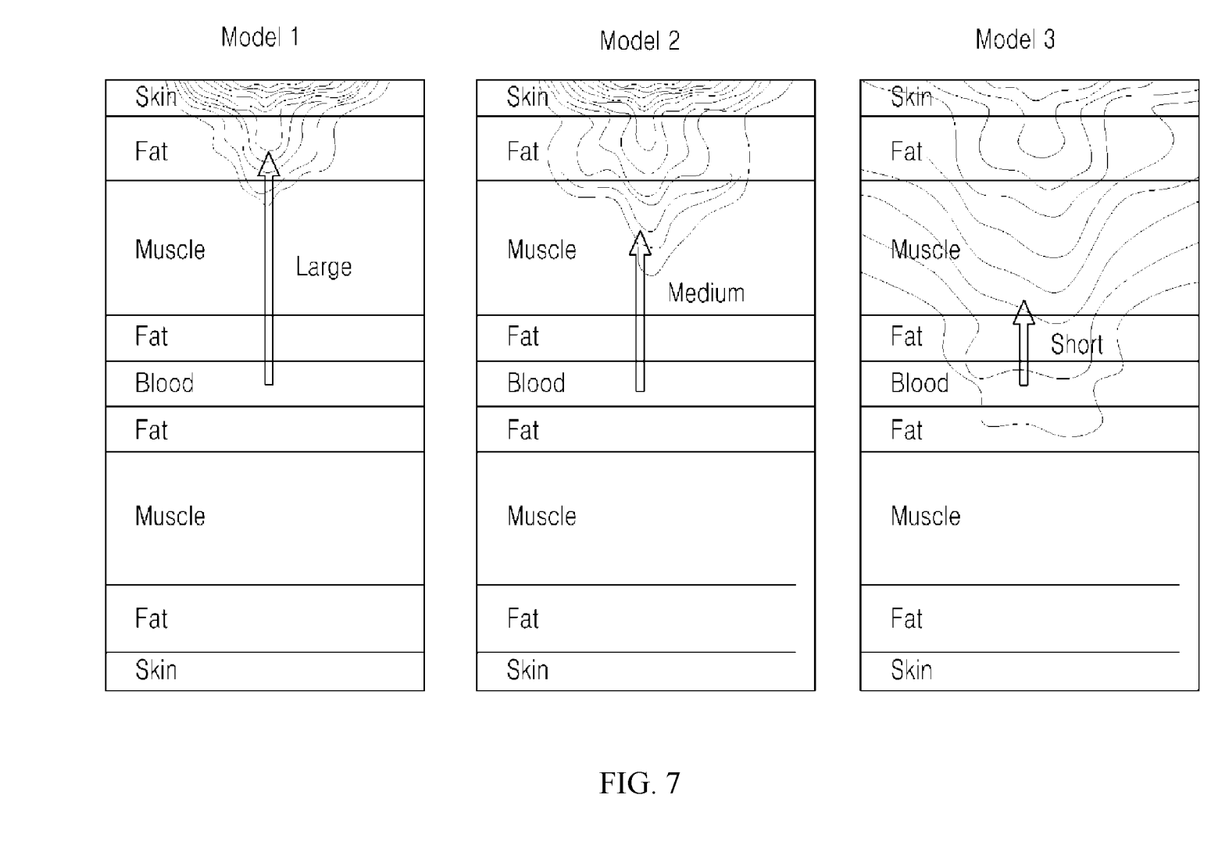
FIG. 7 is a diagram illustrating an electromagnetic wave pattern for each mode, of a blood glucose measurement sensor according to an embodiment of the present disclosure.

FIG. 7 is a diagram illustrating an electromagnetic wave pattern for each mode, of a blood glucose measurement sensor according to an embodiment of the present disclosure. FIG. 7 illustrates examples in which radio waves have reached a subcutaneous layer in the invasive mode, that is, Mode 1, a part of a muscular coat in the single mode, that is, Mode 2, and a blood vessel in the array mode, that is, Mode 3.

Figure 8:
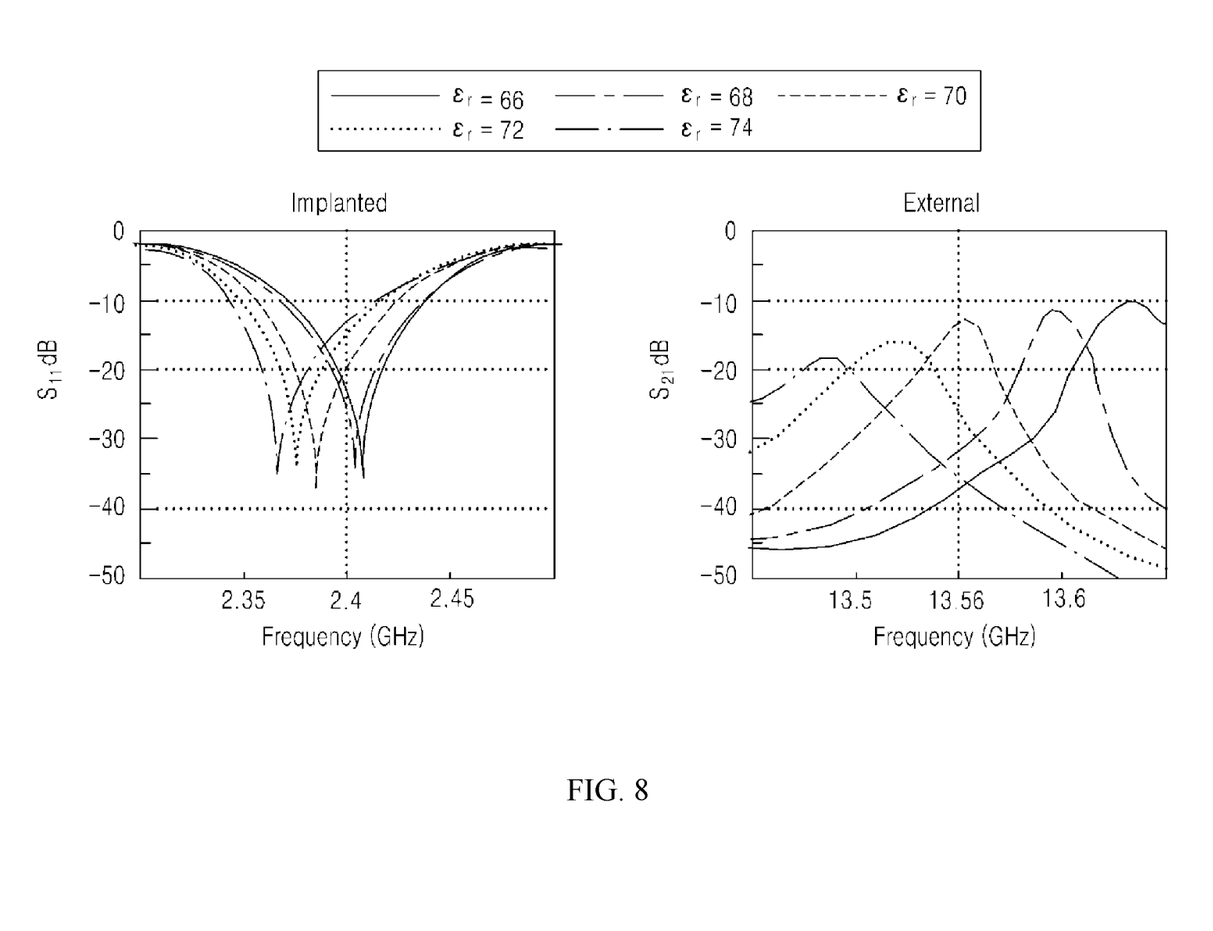
FIG. 8 is graphs illustrating response curves of scattering parameters of the implantable device and the external device in the system for measuring biometric information according to an embodiment of the present disclosure.

FIG. 8 is graphs illustrating response curves of scattering parameters of the implantable device and the external device in the system for measuring biometric information according to an embodiment of the present disclosure. The graphs in FIG. 8 illustrate a change in the resonance frequency in the implantable device 100 and the external device 200 according to a change in biometric information (e.g., blood glucose). A phenomenon in which blood glucose numerical values were lowered when permittivity rose in the implantable device 100 was derived through simulations. When the blood glucose numerical values rise, the permittivity is lowered and the resonance frequency rises.

A frequency generation system for generating a frequency for driving an internal sensor (e.g., the implantable device 100) has a large area. Accordingly, in embodiments of the present disclosure, in order to overcome such a problem, the outside (e.g., the external device 200) may transmit a frequency to an internal sensor.

Such a system for measuring biometric information may use a frequency of 13.56 MHz with respect to the transmission of wireless power and data transmission, but the present disclosure is not limited thereto. Power may be supplied from the external device 200 to the implantable device 100 not having a separate power supply unit, such as a battery, through a wireless power transmission scheme, and may be supplied to the sensor interface 120 of the implantable device 100. The external device 200 may generate a sweeping frequency based on a given interval from a frequency of several GHz for driving the implantable device 100 through the external reader module 400, and may transfer the sweeping frequency to the implantable device 100.

The frequency transferred from the external device 200 to the implantable device 100 may drive the EM-based sensor 110. In this case, the permittivity of the EM-based sensor 110 is changed by a change in blood glucose around the EM-based sensor 110, thereby changing the S-parameter characteristic.

A value of the scattering parameter S11 is lowered in a specific resonance frequency. In order to find the lowest point, the external device 200 sweeps a frequency over a wide band through the external reader module 400, and transfer the swept frequency to the implantable device 100. In each of frequency characteristics reflected by the EM-based sensor 110, a frequency-selective characteristic may be changed and filtered by the frequency-selective filter 124 based on a concentration of a target material (e.g., blood glucose) nearby as in the EM-based sensor 110. Each of the frequencies may be transferred to the envelope detector 122. The envelope detector 122 may find a minimum value. If the size of an output in the envelope detector is too large or small, this may affect the input of the ADC 123. Accordingly, the size of a signal input to the ADC 123 may be adjusted as an input of 30 dB or more through a baseband amplifier (e.g., the amplifier 125). An output adjusted by the baseband amplifier may be input as an input to the ADC 123, may be converted into digital data of 0 and 1, and may be transferred to the external device 200 through a back scattering communication scheme, such as load shift keying (LSK) modulation. The external device 200 may generate data for biometric information by using the digital data transferred by the implantable device 100, and may transfer the generated data to another external device (e.g., a smartphone) through the communication module.

Figure 9:
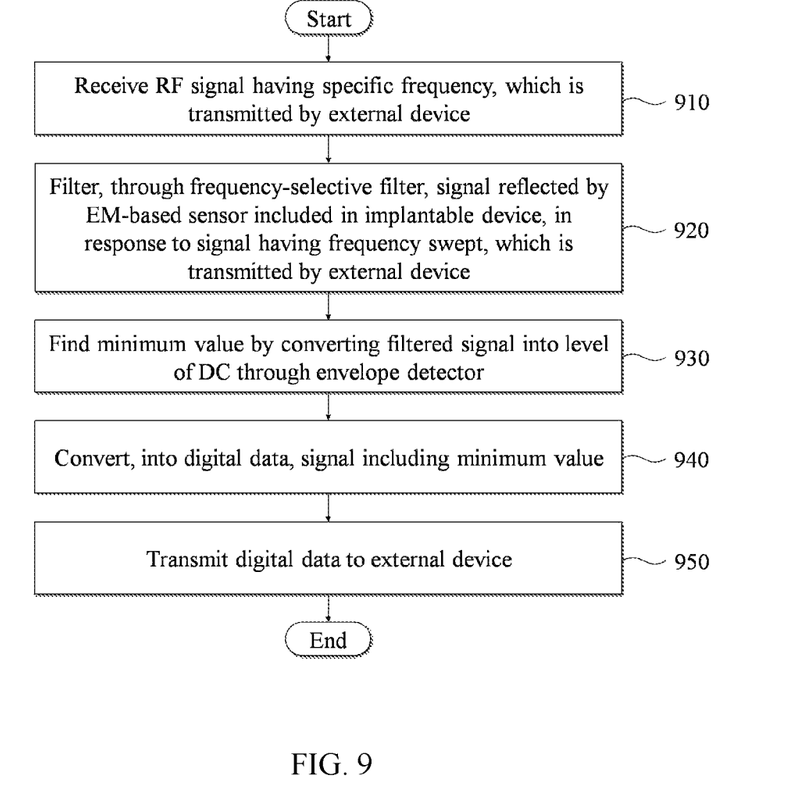
FIG. 9 is a diagram illustrating an example of a method of measuring, by the implantable device, biometric information according to an embodiment of the present disclosure.

FIG. 9 is a diagram illustrating an example of a method of measuring, by the implantable device, biometric information according to an embodiment of the present disclosure. The method of measuring biometric information according to the present embodiment may be performed by the aforementioned implantable device 100.

In step 910, the implantable device 100 may receive an RF signal having a specific frequency, which is transmitted by the external device 200. In this case, the received RF signal may include power that is transmitted through wireless power transmission, and may be used for the driving of the implantable device 100.

In step 920, the implantable device 100 may filter, through the frequency-selective filter 124, a signal reflected by the EM-based sensor 110 included in the implantable device, in response to a signal having a frequency swept, which is transmitted by the external device 200. Blood glucose may be measured based on a characteristic in which a resonance frequency is changed in response to permittivity around the implantable device 100. To this end, the external device 200 may transfer a signal to the implantable device 100 while sweeping the frequency through the phase-locked loop 410. In this case, the implantable device 100 may receive the signal reflected by the EM-based sensor 110, may filter the received signal through the frequency-selective filter 124, and may output signals having the filtered frequency.

In step 930, the implantable device 100 may find a minimum value by converting the filtered signal into a DC level through the envelope detector 122.

In step 940, the implantable device 100 may convert, into digital data, the signal including the minimum value. For example, the implantable device 100 may amplify the size of the signal having the minimum value to a given size or more through the amplifier 125, and may convert the amplified signal into the digital data through the ADC 123.

In step 950, the implantable device 100 may transmit the digital data to the external device 200. As described above, the digital data may be transferred to the external device 200 through the SWIPT IC.

Figure 10:
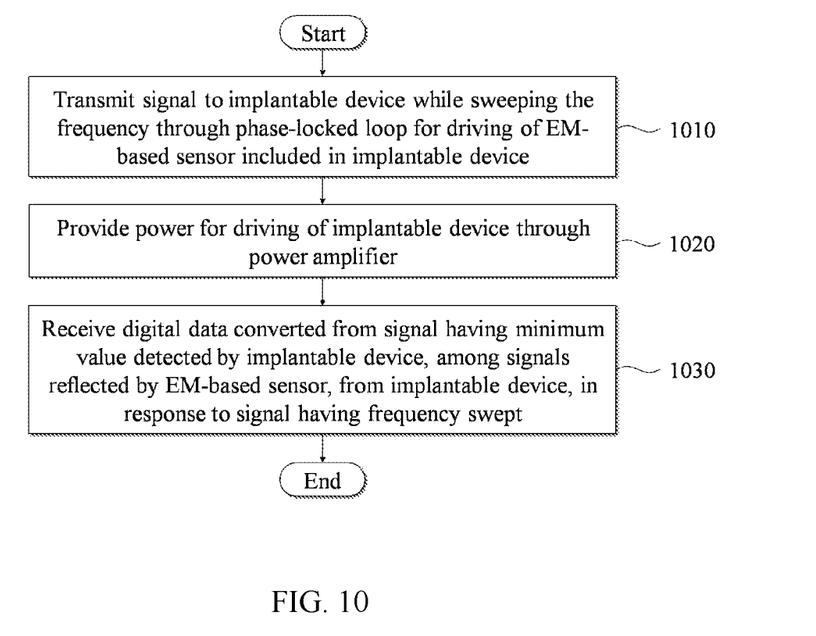
FIG. 10 is a diagram illustrating an example of a method of measuring, by the external device, biometric information according to an embodiment of the present disclosure.

FIG. 10 is a diagram illustrating an example of a method of measuring, by the external device, biometric information according to an embodiment of the present disclosure. The method of measuring biometric information according to the present embodiment may be performed by the aforementioned external device 200.

In step 1010, for the driving of the EM-based sensor 110 included in the implantable device 100, the external device 200 may transmit a signal to the implantable device 100 while sweeping the frequency through the phase-locked loop 410.

In step 1020, the external device 200 may provide power for the driving of the implantable device 100 through the power amplifier. For example, the external device 200 may transmit an RF signal having a specific frequency to the implantable device 100 through the power amplifier 210.

In step 1030, the external device 200 may receive digital data converted from a signal having a minimum value detected by the implantable device 100, among signals reflected by the EM-based sensor 110, from the implantable device, in response to a signal having a frequency swept. In this case, the external device 200 may measure blood glucose based on a characteristic in which a resonance frequency is changed based on permittivity around the implantable device.

In this case, according to embodiments of the present disclosure, blood glucose can be accurately measured by measuring a characteristic change attributable to a change in the blood glucose through the implantable device and the external device.

The aforementioned device may be implemented as a hardware component or a combination of a hardware component and a software component. For example, the device and component described in the embodiments may be implemented using one or more general-purpose computers or special-purpose computers, such as a processor, a controller, an arithmetic logic unit (ALU), a digital signal processor, a microcomputer, a field programmable gate array (FPGA), a programmable logic unit (PLU), a microprocessor, or any other device capable of executing or responding to an instruction. The processing device may perform an operating system (OS) and one or more software applications that are executed on the OS. Furthermore, the processing device may access, store, manipulate, process, and generate data in response to the execution of software. For convenience of understanding, one processing device has been illustrated as being used, but a person having ordinary knowledge in the art may understand that the processing device may include a plurality of processing elements and/or a plurality of types of processing elements. For example, the processing device may include a plurality of processors or one processor and one controller. Furthermore, another processing configuration, such as a parallel processor, is also possible.

Software may include a computer program, a code, an instruction or a combination of one or more of them, and may configure a processing device so that the processing device operates as desired or may instruct the processing devices independently or collectively. The software and/or the data may be embodied in any type of machine, a component, a physical device, or a computer storage medium or device in order to be interpreted by the processing device or to provide an instruction or data to the processing device. The software may be distributed to computer systems that are connected over a network, and may be stored or executed in a distributed manner. The software and the data may be stored in one or more computer-readable recording media.

The method according to an embodiment may be implemented in the form of a program instruction executable by various computer means, and may be stored in a computer-readable medium. The medium may continue to store a program executable by a computer or may temporarily store the program for execution or download. Furthermore, the medium may be various recording means or storage means having a form in which one or a plurality of pieces of hardware has been combined. The medium is not limited to a medium directly connected to a computer system, but may be one distributed over a network. An example of the medium may be one configured to store program instructions, including magnetic media such as a hard disk, a floppy disk and a magnetic tape, optical media such as CD-ROM and a DVD, magneto-optical media such as a floptical disk, ROM, RAM, and a flash memory. Furthermore, other examples of the medium may include an app store in which apps are distributed, a site in which other various pieces of software are supplied or distributed, and recording media and/or storage media managed in a server.

As described above, although the embodiments have been described in connection with the limited embodiments and the drawings, those skilled in the art may modify and change the embodiments in various ways from the description. For example, proper results may be achieved although the aforementioned descriptions are performed in order different from that of the described method and/or the aforementioned elements, such as the system, configuration, device, and circuit, are coupled or combined in a form different from that of the described method or replaced or substituted with other elements or equivalents.

Accordingly, other implementations, other embodiments, and the equivalents of the claims fall within the scope of the claims.

The invention claimed is:

1. A system for measuring biometric information comprising:
   an implantable device inserted into a body and configured to measure biometric information; and
   an external device configured to transmit a signal to the implantable device, wherein the signal's frequency is constantly changing based on a given interval from a frequency of GHz by sweeping a frequency, wherein the external device comprises a phase-locked loop configured to sweep the frequency in order to drive the EM-based sensor included in the implantable device;
   wherein the implantable device comprises:
   an electro-magnetic (EM)-based sensor configured to reflect the signal transmitted by the external device; and a sensor interface configured to measure a power level of the signal reflected and returned by the EM-based sensor and convert the signal into digital data,
wherein the sensor interface comprises:
a frequency-selective filter configured to filter the signal reflected and returned by the EM-based sensor; and
an envelope detector configured to find and output a minimum value in frequencies output by the frequency-selective filter.

2. The system of claim 1, wherein the external device comprises:
a power amplifier configured to provide power for driving the implantable device.

3. The system of claim 2, wherein the external device further comprises a data recovery module configured to recover digital data transferred by the implantable device.

4. The system of claim 2, wherein the external device further comprises a communication module for communicating with another external device.

5. The system of claim 2, wherein the external device further comprises at least one EM-based sensor configured to measure biometric information within a body outside the body.

6. The system of claim 1, wherein the biometric information is measured based on a characteristic in which a resonance frequency is changed in response to permittivity around the implantable device.

7. The system of claim 1, wherein the envelope detector is implemented to convert, into a direct current (DC) level, a signal reflected by S11 of S-parameters and to find a lowest point.

8. The system of claim 1, wherein the sensor interface further comprises:
an amplifier configured to adjust a size of the output of the envelope detector to a preset size or more; and
an analog-digital converter (ADC) configured to receive an output of the amplifier and convert the output into the digital data.

9. The system of claim 1, wherein:
the external device comprises a wireless power transmitter for transmitting wireless power to the implantable device, and
the implantable device comprises a wireless power receiver for receiving wireless power transmitted by the external device.

* * * * *